(12) United States Patent
U'Ren

(10) Patent No.: US 9,395,367 B1
(45) Date of Patent: Jul. 19, 2016

(54) METHOD TO IDENTIFY ANTIGEN-SPECIFIC B CELLS FOR ANTIBODY DEVELOPMENT

(71) Applicant: RareCyte, Inc., Seattle, WA (US)

(72) Inventor: Lance U'Ren, Seattle, WA (US)

(73) Assignee: RareCyte, Inc., Seattle, WA (US)

( * ) Notice: Subject to any disclaimer, the term of this patent is extended or adjusted under 35 U.S.C. 154(b) by 0 days.

(21) Appl. No.: 15/056,809

(22) Filed: Feb. 29, 2016

(51) Int. Cl.
- *A61K 38/00* (2006.01)
- *G01N 33/68* (2006.01)
- *C12P 21/06* (2006.01)
- *C12N 5/10* (2006.01)
- *G01N 33/569* (2006.01)

(52) U.S. Cl.
CPC ............................... *G01N 33/56966* (2013.01)

(58) Field of Classification Search
None
See application file for complete search history.

(56) References Cited

U.S. PATENT DOCUMENTS

| | | |
|---|---|---|
| 5,326,696 A | 7/1994 | Chang |
| 5,627,052 A | 5/1997 | Schrader |
| 6,541,225 B1 | 4/2003 | Li |
| 8,945,857 B2 | 2/2015 | Schrader |
| 2004/0219611 A1 | 11/2004 | Racher |
| 2006/0148012 A1 | 7/2006 | Brown et al. |

OTHER PUBLICATIONS

C. Langsdorf et al., Illuminating Endocytosis with Targeted pH-sensitive Fluorescent Compounds, ASCB 2013 Poster B1994, Life Technologies.

*Primary Examiner* — Michail Belyavskyi

(57) ABSTRACT

This disclosure is directed to methods for retrieving and using at least one lymphocyte. Additionally, cell receptor sequences identified with this strategy could be used for antibody development.

17 Claims, 1 Drawing Sheet

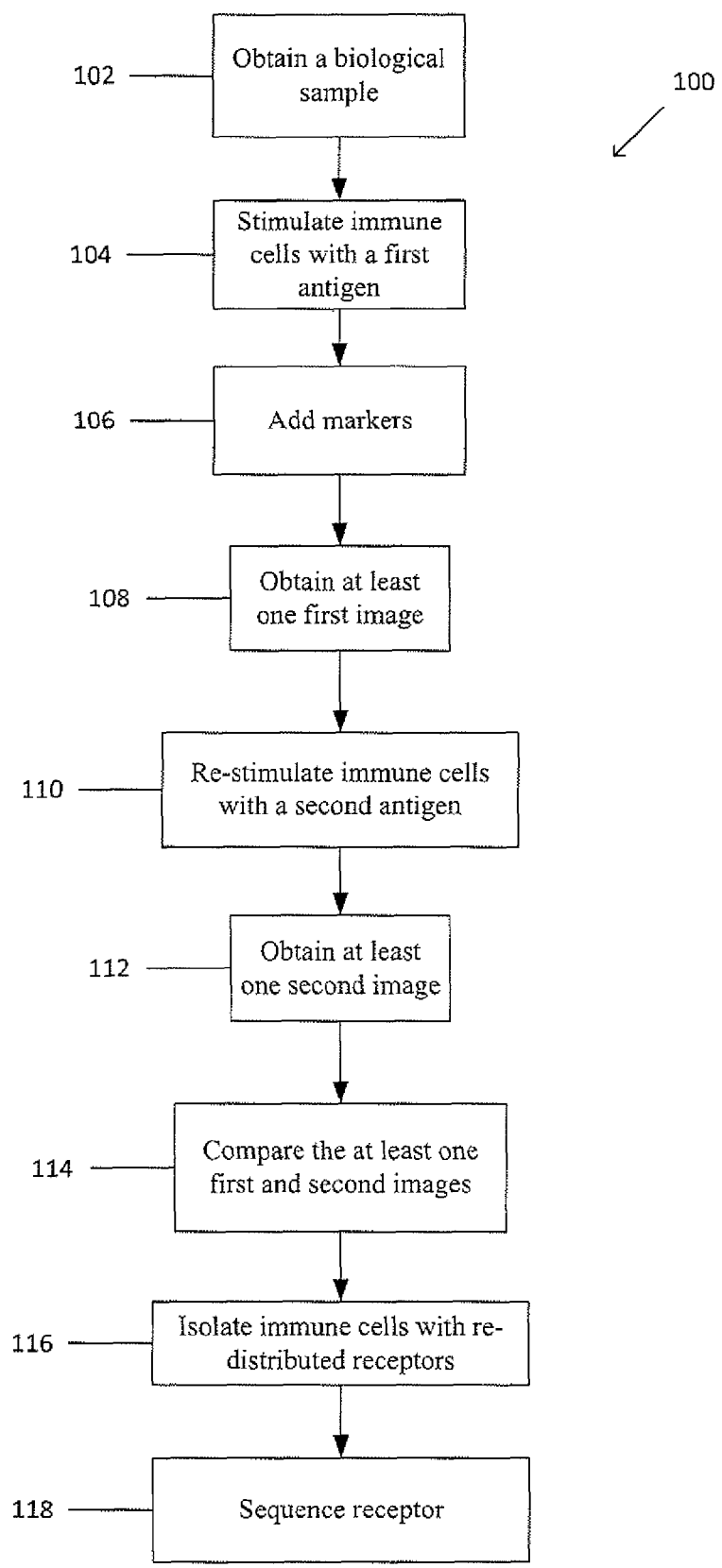

METHOD TO IDENTIFY ANTIGEN-SPECIFIC B CELLS FOR ANTIBODY DEVELOPMENT

TECHNICAL FIELD

This disclosure relates generally to retrieving lymphocytes, such as B cells, T cells, and plasma cells and in particular, to isolating and sequencing antigen-specific lymphocytes.

BACKGROUND

T cells and B cells express specialized receptors which can recognize and respond to very specific protein or peptide sequences, called T Cell Receptors (TCRs) and B Cell Receptors (BCRs) respectively. The activation of lymphocytes is an essential physiological response to fight off infections. Determining an individual's naïve and/or memory B or T cell count, such that the cells are specific for an particular antigen or peptide, may aid in determining the individual's response to a given therapy contain said antigen. Alternatively, an individual's naïve precursor count may aid in predicting the individual's response to a given antigen or peptide, as would be the case with a vaccine. Furthermore, it may be desirous to be able to interrogate the native BCR repertoire to generate a fully human monoclonal antibody.

DESCRIPTION OF THE DRAWINGS

FIG. 1 shows an example method for retrieving and using immune cells.

DETAILED DESCRIPTION

This disclosure is directed to methods for retrieving and using at least one lymphocyte. Additionally, cell receptor sequences identified with this strategy could be used for antibody development.

For the sake of convenience, the method below is described with reference to at least one immune cell, such as a lymphocyte. But the method described below is not intended to be so limited in its scope of application and may be used for plasma cells, naïve B cells, memory B cells, naïve T cells, or memory T cells. The method may also be used with another appropriate biological analyte. Additionally, the method may be used for any number of cells or analytes, such as one, at least one, a plurality, etc.

Additionally, for the sake of convenience, the methods are described with reference to a sample of blood. But the methods described below are not intended to be so limited in their scope of application. The methods, in practice, may be used with any kind of suspension, solution, or fluid. For example, a sample may be urine, blood, buffy coat, red blood cells, plasma, bone marrow, cystic fluid, ascites fluid, stool, semen, cerebrospinal fluid, nipple aspirate fluid, saliva, amniotic fluid, vaginal secretions, mucus membrane secretions, aqueous humor, vitreous humor, vomit, lymphoid tissue suspension, and any other physiological fluid or semi-solid. The method may also be used with another appropriate solution or suspension.

FIG. 1 shows a flow diagram of an example method 100 for retrieving and using immune cells. In block 102, a biological sample, such as blood, suspected of containing immune cells including receptors is obtained, such as by venipuncture.

In block 104, a first antigen is added to the biological sample to stimulate the immune cells, such as by re-distributing the receptors. The receptors, for example, may be endocytosed. In addition to the re-distribution of the receptors, the antigen may cause co-localization of the receptors and at least one lysosome. The lysosome may also be labeled with a fluorescent probe, though with a different fluorescent molecule than the receptors. Alternatively, the receptors may undergo capping or be expelled.

After adding the first antigen, an excess of the first antigen may be washed away. The immune cells may then be incubated with the remaining first antigen. The incubation time may last any appropriate time, such as up to 24 hours, including, 1 hour, 2, hours, 4 hours, 12 hours, etc. The incubation may allow the receptors of the immune cells to return to the receptors' original location relative to the immune cells, such as on the outer surface of the immune cells.

In block 106, fluorescent probes may be added to the sample to label the immune cells and/or the receptors (i.e. receptor probes). The fluorescent probes, for example, may be used to label the immune cells, thereby providing a fluorescent signal for identification and characterization. The fluorescent probe may include a fluorescent molecule bound to a ligand. Ligands can be used to highlight and classify the immune cells present in the suspension by conjugating ligands that attach to particular receptors or biomarkers with a particular fluorescent molecule. Additionally, the fluorescent probes may include activation markers to determine that the immune cells have been activated or stimulated. For example, the fluorescent molecules may include, but are not limited to pH-sensitive dyes, such as pHrodo® (ThermoFisher), CypHER5E (GE), 2',7'-bis(2-carboxyethyl)-5(6)-carboxyfluorescein tetrakis(acetoxymethyl) ester (BCECF AM), 5(6)-carboxy-2',7'-dichlorofluorescein, 5(6)-carboxyfluorescein, 5(6)-carboxyfluorescein diacetate, 5(6)-carboxyfluorescein N-hydroxysuccinimide ester, 3,6-diacetoxyphthalonitrile, 6,8-dihydroxy-1,3-pyrenedisulfonic acid disodium salt, Eosin diacetate, and naphthofluorescein; quantum dots; commercially available dyes, such as fluorescein, FITC ("fluorescein isothiocyanate"), R-phycoerythrin ("PE"), Texas Red, allophycocyanin, Cy5, Cy7, cascade blue, Hoechst, DAPI ("4',6-diamidino-2-phenylindole") and TRITC ("tetramethylrhodamine isothiocyanate"); combinations of dyes, such as CY5PE, CY7APC, and CY7PE; and synthesized molecules, such as self-assembling nucleic acid structures. The pH-sensitive dye may fluoresce in an acidic environment but not fluoresce in a basic environment. Alternatively, the pH-sensitive dye may fluoresce in a neutral or basic environment but not fluoresce in an acidic environment.

In block 108, a first image or first set of images (collectively, the "first images") are obtained by imaging. The first images may depict the immune cells having been activated or stimulated, though with receptors that have returned to the receptors' original location relative to the immune cells.

To image the immune cells, the sample is illuminated with one or more wavelengths of excitation light from a light source, such as red, blue, green, and ultraviolet. The imaging may be done with a microscope, such as a fluorescent microscope, a scanner, or the like. Imaging may be done in fluorescence, bright field, or dark field. The images formed from the emission light of each fluorescent molecule can be overlaid when a plurality of fluorescent molecules are excited and emit light. The images may then be analyzed to detect, locate, and characterize the immune cells. Imaging may be performed in a tube, on a microscope slide, or in any appropriate vessel or substrate for imaging.

In block 110, a second antigen is added to the biological sample to re-stimulate the immune cells, thereby re-distributing the receptors. The receptors, for example, may be endocytosed. In addition to the re-distribution of the receptors, the antigen may cause co-localization of the receptors and at least one lysosome. The lysosome may also be labeled with a fluorescent probe, though with a different fluorescent molecule than the receptors. Alternatively, the receptors may undergo capping or be expelled.

Alternatively, the first images may be obtained after adding the second antigen and before obtaining the second images, as the second antigen may not immediately cause re-distribution of the receptors. The first images may be obtained within a given time frame after adding the second antigen (i.e. up to 4 hours, including 30 minutes, 60 minutes, 90 minutes, and hours). For example, the first images may be obtained 5 minutes after adding the second antigen, then the sample may be allow to incubate with the second antigen to provide ample time to re-stimulate the immune cells. The second images may be then be obtained.

In block 112, a second image or second set of images (collectively, the "second images") are obtained by imaging. The second images may depict the re-distributed receptors after re-stimulation in response to the second antigen. Optionally, a third image or third set of images (collectively, the "third images") are obtained by imaging after a given amount of time has elapsed after obtaining the second images. Changes in mean fluorescent intensity of fluorescent probes between the second and third images may be calculated to determine antibody affinity.

In block 114, the first and second images are compared to dump and retain cells or analytes (i.e. determine that the receptors were re-distributed in response to the second antigen added during the re-stimulating step), such as by image analysis. Any cell or analyte from the second image(s) that appears identical or substantially similar to the first image(s) of the same cell or analyte may be dumped (i.e. where the receptors were not re-distributed in response to the second antigen). Any cell or analyte from the second image(s) that do not appear identical or substantially similar to the first image(s) taken of the same cell or analyte may be retained (i.e. where the receptors were re-distributed in response to the second antigen). For example, cells that endocytosed receptors in the first images are dumped (i.e. no longer considered or removed from consideration) as those cells may be the result of non-specific staining or were already activated prior to the addition of the first antigen. Additionally, co-localization of the immune cell receptor and at least one lysosome may be compared, when it is desirous to do so.

In block 116, the immune cells are retrieved from the rest of the sample. To retrieve the immune cells, the immune cells may undergo enrichment and/or isolation. The immune cells may be enriched by any appropriate enrichment process including, but not limited to, sequential density fractionation, magnetic-activated cell sorting, fluorescence-activated cell sorting, differential lysis, depletion filters, or the like. Sequential density fractionation is a process by which a sample is divided into fractions or a fraction of a sample is divided into sub-fractions by a step-wise or sequential process, such that each step or sequence results in the collection or separation of a different fraction or sub-fraction from the preceding and successive steps or sequences. In other words, sequential density fractionation provides individual sub-populations of a population or individual sub-sub-populations of a sub-population of a population through a series of steps. For example, separation fluids may be used whereby each separation fluid has a different density, thereby separating a fraction of a sample into sub-fractions based on the densities of the respective sub-fractions via the different density separating fluids. The immune cells may be isolated from rest of the sample, whether with or without prior enrichment, by selecting at least one immune cell at a time with any appropriate device or system for picking a cell. Imaging the sample or a portion thereof, as discussed above, may be performed to aid in isolation by providing location and characterization information for isolation purposes. Enrichment or isolation may also act to identify at least one immune cell, whether it is already-stimulated, unstimulated, or newly stimulated.

In block 118, the isolated immune cells undergo sequencing. The immune cell receptor on the immune cell may be analyzed and sequenced using any appropriate method or technique, though more specifically extracellular and intracellular analysis including intracellular protein labeling; nucleic acid analysis, including, but not limited to, DNA arrays, expression arrays, protein arrays, and DNA hybridization arrays; in situ hybridization ("ISH"—a tool for analyzing DNA and/or RNA, such as gene copy number changes); polymerase chain reaction ("PCR"); reverse transcription PCR; or branched DNA ("bDNA"—a tool for analyzing DNA and/or RNA, such as mRNA expression levels) analysis. Sequencing may be done on the entire genome or cDNA may be synthesized from mRNA, such as by reverse transcriptase.

After properly sequencing the receptors, the receptor sequence may then be used to develop antibodies against respective antigens, such as for fully human monoclonal antibody production. Alternatively, the screening step may be used to identify patients who may have adverse reactions (i.e. autoimmune response) to the suggested therapies or to identify patients who are more likely to respond to a therapy (i.e. vaccination).

The methods can be modified for use as a T cell receptor (TCR) discovery platform by similarly following the endocytosis of TCRs following peptide or protein stimulation and comparing against the pre-stimulation images.

Example Method

1. Collect sample (blood, bone marrow, or tissue)
2. (Optional) Isolate target material (buffy coat or tissue digest)
3. (Optional) Immune cell enrichment
    a. Magnetic or bead/weight separation
    b. Fluorescent activated cell sorting (FACS)
    c. Rosetting non-target cells with tetrameric antibodies
    d. Sequential density fractionation (SDF)
4. Stimulate immune cells with first antigen
    a. Pulse first antigen
5. (Optional) Wash away excess first antigen
6. (Optional) Incubate immune cells with first antigen
7. Add antibody cocktail for labeling
    a. Add activation markers to label immune cells
    b. Add receptor probes to label immune cell receptors
    c. Add additional antibody-dye complexes to confirm or characterize immune cells
        i. CD19, CD20, maturation markers
        ii. BCR isotype (IgG1, IgG2a, IgG2b, IgM, IgA)
        iii. Nuclear (DAPI, Cytox Orange, Syto 9)
        iv. Exclusion markers (CD14, CD66b, CD15, CD3)
8. Incubate antibody cocktail
    a. 0-45° C.
    b. Up to approximately 24 hours (e.g. 1 hour)
9. Place labeled cells on substrate for imaging and/or archiving
10. Obtain First Image(s)
11. Adding a second antigen to re-stimulate immune cells with a. The second antigen may be identical to the first antigen
b. Alternatively, the second antigen may be substantially similar, though not identical to, the first antigen
12. Obtain Second Image(s)
13. (Optional) Obtain Third Image(s) after a given amount of time has elapsed after obtaining the Second Image(s)
    a. Determine change(s) in mean fluorescent intensity of markers Second and Third Images
    b. Determine antibody affinity based on change(s) in mean fluorescent intensity
14. Compare First and Second Image(s) to retain and dump cells or analytes, such as by image analysis
    a. Dump any cell or analyte from the Second Image(s) that appears identical or substantially similar to the First Image(s) of the same cell or analyte
        i. For example, where the receptors were not re-distributed in response to the second antigen
    b. Retain cell or analyte from the Second Image(s) that do not appear identical or substantially similar to the First Image(s) taken of the same cell or analyte
        i. For example, where the receptors were re-distributed in response to the second antigen
15. Isolate retained immune cells
16. Obtain RNA or DNA of the receptors
17. Sequence the receptors
    a. Entire genome
    b. cDNA
        i. Synthesize cDNA from mRNA
            1. Using reverse transcriptase
18. Use receptor sequence for antibody development
    a. Fully human antibody The foregoing description, for purposes of explanation, used specific nomenclature to provide a thorough understanding of the disclosure. However, it will be apparent to one skilled in the art that the specific details are not required in order to practice the systems and methods described herein. The foregoing descriptions of specific embodiments are presented by way of examples for purposes of illustration and description. They are not intended to be exhaustive of or to limit this disclosure to the precise forms described. Many modifications and variations are possible in view of the above teachings. The embodiments are shown and described in order to best explain the principles of this disclosure and practical applications, to thereby enable others skilled in the art to best utilize this disclosure and various embodiments with various modifications as are suited to the particular use contemplated. It is intended that the scope of this disclosure be defined by the following claims and their equivalents:

I claim:

1. A method comprising:
   collecting a sample suspected of containing at least one B cell comprising at least one B Cell Receptor ("BCR");
   stimulating the at least one B cell with a first aliquot of an antigen;
   washing away any excess antigen of the first aliquot;
   labeling the at least one BCR with at least one receptor probe comprising a fluorescent molecule bound to a ligand, wherein the ligand is bound to the at least one BCR;
   imaging the sample to obtain at least one first image;
   re-stimulating the at least one B cell with a second aliquot of the antigen;
   re-imaging the sample to obtain at least one second image;
   comparing the at least one first image and the at least one second image to determine that the at least one B cell was re-stimulated in response to the second aliquot of the antigen;
   isolating the at least one B cell that has been re-stimulated;
   sequencing the at least one BCR from said cell; and
   generating a monoclonal antibody based on the sequence of said the at least one BCR.

2. The method of claim 1, wherein the isolating and sequencing steps are performed after the comparing step.

3. The method of claim 2, wherein the imaging and re-imaging steps are performed with a fluorescent microscope.

4. The method of claim 3, wherein the comparing step is performed by image analysis.

5. The method of claim 1, wherein the sequence is an entire receptor genome.

6. The method of claim 1, wherein the sequence is cDNA.

7. The method of claim 1, further comprising the step of:
   synthesizing cDNA from mRNA of the at least one BCR.

8. The method of claim 1, further comprising the step of:
   disregarding any cell from the at least one second image that is identical or substantially similar to the at least first image of the same cell; and
   noting the at least one B cell from the at least one second image that is not identical or substantially similar to the at least first image of the same at least one B cell,
   wherein the comparing, disregarding, and noting steps are performed by image analysis.

9. The method of claim 8, wherein the disregarding and retaining steps are performed after the comparing step and before the isolating step.

10. The method of claim 1, wherein the at least one fluorescent molecule is a pH-sensitive dye.

11. The method of claim 1, further comprising the step of:
    labeling the at least one B cell with at least one activation marker.

12. The method of claim 1, wherein none of the fluorescent molecules is a pH-sensitive dye.

13. The method of claim 1, further comprising the step of:
    incubating the sample with the first aliquot of the antigen,
    wherein the incubating step occurs after the washing step and before the labeling step.

14. The method of claim 1, wherein the imaging step is performed after the labeling step and before the re-stimulating step; and wherein the re-imaging step is performed after the re-stimulating step and before the comparing step.

15. The method of claim 13, wherein the incubating step is performed for up to 24 hours.

16. The method of claim 1, further comprising the step of placing the sample on a slide before the imaging step.

17. The method of claim 1, wherein the monoclonal antibody is fully human.

* * * * *